United States Patent [19]

Kitchin et al.

[11] Patent Number: 4,880,801
[45] Date of Patent: Nov. 14, 1989

[54] HETEROCYCLIC AMINO COMPOUNDS

[75] Inventors: John Kitchin, Eastcote; Peter C. Cherry, South Harrow; Adrian J. Pipe; Andrew J. Crame, both of Greenford; Alan D. Borthwick, London, all of England

[73] Assignee: Glaxo Group Limited, London, England

[21] Appl. No.: 198,971

[22] Filed: May 26, 1988

Related U.S. Application Data

[63] Continuation of Ser. No. 930,891, Nov. 17, 1986, abandoned, which is a continuation of Ser. No. 726,604, Apr. 24, 1985, abandoned.

[30] Foreign Application Priority Data

Apr. 24, 1984 [GB] United Kingdom ............... 8410456
Feb. 15, 1985 [GB] United Kingdom ............... 8503975

[51] Int. Cl.$^4$ ..................... A61K 31/55; A61K 31/40; C07D 209/56
[52] U.S. Cl. .................................. 514/215; 514/411; 548/430
[58] Field of Search ................. 548/430; 514/411, 215

[56] References Cited

U.S. PATENT DOCUMENTS 4,496,579 1/1985 Crame et al. ..................... 514/411
4,680,411 7/1987 Picart ............................. 514/411

OTHER PUBLICATIONS

A. Burger, Medicinal Chemistry (Second Edition), pp. 42–43 (1960), Interscience Publishers, Inc. N.Y. RS403B8.
A. Funke et al., Chem. Abstr. vol. 56, No. 14257i (1962).
G. Marini–Bettolo, Chem. Abstr. vol. 52, No. 16356h (1958).
R. Berthold et al., Helvetica Chimica Acta, 55:2461–2467, (1977).

Primary Examiner—Mary E. Ceperley
Attorney, Agent, or Firm—Morgan & Finnegan

[57] ABSTRACT

Compounds of the general formula (I)

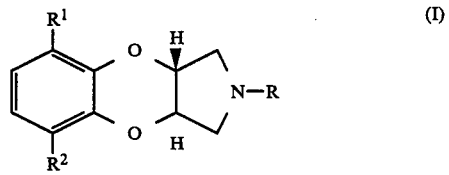

(R is H, alkyl, alkenyl, alkynyl, cycloalkyl, aralkyl or CHO, $R^1$ and $R^2$ are independently halogen, alkyl, alkoxy, hydroxyl, cyano, nitro or $-NR^3R^4$ where $R^3$ and $R^4$ are independently H or alkyl and $R^2$ may be H) and their salts have selective $\alpha_2$-adrenoreceptor antagonist action.

The compounds may be prepared by amination of compounds of the general formula (II)

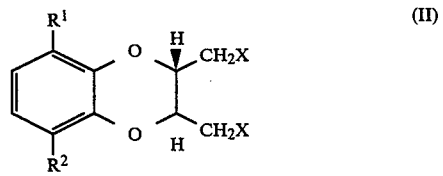

(where $R^1$ and $R^2$ are as defined above and X is a leaving group.

15 Claims, No Drawings

HETEROCYCLIC AMINO COMPOUNDS

This is a continuation of co-pending application Ser. No. 930,891 filed Nov. 17, 1986, now abandoned which is a continuation of application Ser. No. 726,604 filed Apr. 24, 1985, now abandoned.

This invention relates to heterocyclic amino compounds. More specifically this invention relates to benzodioxinopyrrole derivatives, to processes for the preparation thereof, to pharmaceutical preparations containing them, and to their use in medicine.

The alpha ($\alpha$)-adrenoreceptors of the sympathetic nervous system are classified pharmacologically into two sub-groups, namely $\alpha_1$ and $\alpha_2$. The $\alpha_2$-type are situated predominantly on the presynaptic terminals of noradrenergic neurones and are activated by the released neurotransmitter. Such activation results in a diminished release of noradrenaline on subsequent stimulation of the neurones, the $\alpha_2$-adrenoreceptors thus forming part of an autoinhibitory feedback mechanism for regulating the synaptic concentration of the neurotransmitter. A selective $\alpha_2$-adrenoreceptor antagonist would be expected to produce an increase in the synaptic concentrations of noradrenaline by blocking the autoinhibitory feedback mechanism and would thus be of potential value in human medicine for the treatment of disorders such as depression which are associated with a deficiency of noradrenaline at postsynaptic adrenoreceptors.

$\alpha_2$-Adrenoreceptors also occur at non-neuronal sites such as on blood-platelets, in pancreatic islet cells, on adipocytes and in the proximal tubules of the kidney. Activation of $\alpha_2$-adrenoreceptors at these sites lead to platelet aggregation, inhibition of insulin release, inhibition of lipolysis and retention of sodium respectively.

A selective $\alpha_2$-adrenoreceptor antagonist thus has a potential therapeutic use as an antidepressant either alone or in a complimentary combination with an established antidepressant, and in either treating or preventing conditions such as migraine, thrombosis, diabetes, obesity, hypertension, constipation, paralytic ileus and senile dementia.

We have now found that the compounds of formula (I) below and their physiologically acceptable salts have a selective $\alpha_2$-adrenoreceptor antagonist action.

The invention thus provides compounds of general formula (I)

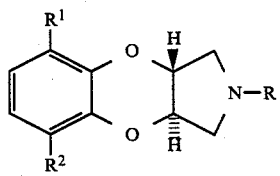

wherein

R is a hydrogen atom or a group selected from $C_{1-6}$ alkyl (optionally substituted by $C_{3-7}$ cycloalkyl), $C_{3-6}$ alkenyl, $C_{3-6}$ alkynyl, $C_{3-7}$ cycloalkyl, aralkyl (in which the alkyl moiety contains 1-5 carbon atoms) and —CHO;

$R^1$ is a halogen atom or a group selected from $C_{1-4}$ alkyl, $C_{1-4}$ alkoxy, hydroxyl, cyano, nitro and —$NR^3R^4$ where $R^3$ and $R^4$ is each a hydrogen atom or a $C_{1-4}$ alkyl group; and $R^2$ is a hydrogen atom, a halogen atom or is a group as defined above for $R^1$;

and the physiologically acceptable salts and hydrates thereof.

In general formula (I), the alkyl, alkenyl and alkynyl groups represented by R, $R^1$ and $R^2$ may be straight or branched chain groups.

When R contains a —C=C— or —C≡C— linkage this is not directly attached to the nitrogen atom. When R is alkyl it may be, for example, methyl, ethyl or propyl, methyl being preferred. When R is an alkyl group substituted by a $C_{3-7}$ cycloalkyl group it may be, for example, cyclopropyl $C_{1-3}$ alkyl such as cyclopropylmethyl. When R is alkenyl it may be, for example, allyl and when R is alkynyl it may be, for example, propynyl. When R is cycloalkyl it may be, for example, cyclopropyl. When R is an aralkyl group it may be, for example phen$C_{1-5}$alkyl, such as benzyl.

The halogen atoms represented by $R^1$ and $R^2$ may be fluorine, chlorine, bromine or iodine atoms. Examples of alkyl and alkoxy groups represented by $R^1$ and $R^2$ are methyl, ethyl, methoxy and ethoxy groups. The group —$NR^3R^4$ may be, for example, an amino, methylamino, ethylamino, dimethylamino or diethylamino group.

Suitable physiologically acceptable salts are the acid addition salts formed with inorganic acids, for example hydrochlorides, hydrobromides, phosphates and sulphates, and with organic acids, for example citrates, tartrates, acetates, maleates and succinates. The hydrochlorides are particularly useful.

It will be appreciated that each compound of general formula (I) is a trans isomer and exists as two enantiomers. The structural formulae herein are to be understood to depict either enantiomer of each compound as well as mixtures of the enantiomers, including racemates, even through the precise structure as set out only relates to one enantiomer.

A preferred group of compounds of general formula (I) is that wherein R is a hydrogen atom. Another preferred group of compounds of general formula (I) is that wherein R is a $C_{1-3}$ alkyl group, particularly a methyl or ethyl group.

In a further preferred group of compounds of formula (I) $R^1$ is a halogen atom or a $C_{1-4}$ alkyl or $C_{1-4}$ alkoxy group, in particular a chlorine or fluorine atom or a methyl or methoxy group.

A further preferred group of compounds of formula (I) is that in which $R^2$ is a hydrogen or fluorine atom, particularly a hydrogen atom.

Particularly important compounds of formula (I) are those in which R is a hydrogen atom or a methyl or ethyl group, particularly a hydrogen atom; $R^1$ is a chlorine or fluorine atom or a methyl or methoxy group, particularly a chlorine or fluorine atom and especially a fluorine atom; and $R^2$ is a hydrogen or fluorine atom, especially a hydrogen atom.

Important compounds are ($\pm$)-trans-2,3,3a,9a-tetrahydro-5-methyl-1H-[1,4]benzodioxino[2,3-c]pyrrole, and its 3aS- and 3aR-isomers; ($\pm$)-trans-5-chloro-2,3,3a,9a-tetrahydro-1H-[1,4]benzodioxino[2,3-c]pyrrole, and its 3aS- and 3aR-isomers; ($\pm$)-trans-5,8-difluoro-2,3,3a,9a-tetrahydro-1H-[1,4]benzodioxino[2,3-c]pyrrole and its 3aS- and 3aR-isomers; and their physiologically acceptable salts and hydrates, particularly the hydrochlorides.

Particularly important compounds, by virtue of their especially useful biological profiles, are ($\pm$)-trans-5-fluoro-2,3,3a,9a-tetrahydro-1H-[1,4]benzodioxino[2,3- c]pyrrole and its 3aS- and 3aR-isomers and their physiologically acceptable salts and hydrates, particularly the hydrochlorides.

The compounds of the invention have selective $\alpha_2$-adrenoreceptor antagonist action. The test for determining the $\alpha_2$-adrenoreceptor antagonist action is based on the ability to prevent the action of the selective $\alpha_2$-adrenoreceptor agonist such as clonidine or 5-bromo-N-(4,5-dihydro-1H-imidazol-2-yl)-6-quinoxalinamine, [R-(R*R*)]-2,3-dihydroxybutanedioate (UK 14304-18) on the rat field stimulated vas deferens preparation.

Clonidine and UK 14304-18 inhibit the twitch response of the rat isolated vas deferens to low frequency motor nerve stimulation. This inhibition is a consequence of activation of presynaptic adrenoreceptors of the $\alpha_2$-type. Antagonism of the effect of clonidine or UK 14304-18 is quantified by measuring the parallel shift to the right of the inhibitory $\alpha_2$-adrenoreceptor agonist $\log_{10}$ (concentration)/response curve in the presence of increasing concentrations of the antagonist. Potency and competitiveness of antagonism are determined by the method of Arunlakshana & Schild (Br. J. Pharmac. 1959, 14 48–58).

The $\alpha$-adrenoreceptor-type selectivity of the compounds of general formula (I) is similarly assessed by measuring the ability to produce a parallel shift to the right of the $\log_{10}$ (concentration)/response curve for the $\alpha_1$-adrenoreceptor agonist phenylephrine. The $\alpha_1$-adrenoreceptor-mediated responses of phenylephrine measured were contractions of the rat isolated anococcygeus muscle (Leighton, Butz & Parameter, Eur. J. Pharmac., 1979, 58 27–38).

The compounds of the invention are thus of interest in the treatment or prevention of migraine, thrombosis, diabetes, obesity, hypertension, constipation, paralytic ileus and senile dementia, and in particular for the treatment of depression.

According to a further aspect, the invention provides compounds of general formula (I) and their physiologically acceptable salts for use in the therapy or prophylaxis of migraine, thrombosis, diabetes, obesity, hypertension, constipation, paralytic ileus and senile dementia and in particular depression. The compounds of the invention may be used either alone or with an additional active ingredient. Thus, for example, in the treatment of depression, the compound of the invention may be used alone, or may be co-administered with an established antidepressant (e.g. desmethylimipramine, imipramine or amitriptyline) either in a single formulation or in separate formulations. The established antidepressant can be used in accordance with conventional practice.

The compounds according to the invention may be formulated in a conventional manner, optionally together with one or more other active ingredients, for administration by any convenient route for example for oral, rectal, intravenous or intramuscular administration. Oral administration is preferred.

Thus according to another aspect, the invention provides a pharmaceutical composition comprising a compound of general formula (I) and/or a physiologically acceptable salt thereof together with a physiologically acceptable carrier or excipient. The composition may optionally contain an additional active ingredient, for example an antidepressant such as desmethylimipramine, imipramine or amitriptyline.

For oral administration, the pharmaceutical composition may take the form of, for example, tablets, capsules, powders, solutions, syrups or suspensions prepared by conventional means with physiologically acceptable excipients.

Compositions for rectal administration may be in the form of suppositories using a conventional suppository excipient.

The compounds may be formulated for intravenous or intramuscular administration in dry form for reconstitution before use, or as a sterile solution or suspension.

A proposed daily dose for administration to man is 0.01 to 10 mg/kg, for example 0.05 to 3 mg/kg, which may be conveniently administered in 1 to 3 doses per day. The precise dose administered will of course depend on the age and condition of the patient. The daily dosage may conveniently be administered in the form of dosage units, each unit containing for example 0.01 to 3 mg/kg of active ingredient.

The compounds according to the invention may be prepared by a number of processes. In the following description the groups, R, $R^1$ and $R^2$ are as previously defined for general formula (I) except where otherwise indicated.

It will be appreciated that certain of the reactions described below are capable of affecting other groups in the starting material (e.g. nitro, cyano) which are desired in the end product; care must therefore be taken in accordance with conventional practice, either to use reaction conditions under which such groups remain substantially inert, or to perform the reaction as part of a sequence which avoids its use when such groups are present in the starting material.

According to a first example (A), a compound of general formula (I) may be prepared by amination of a compound of general formula (II).

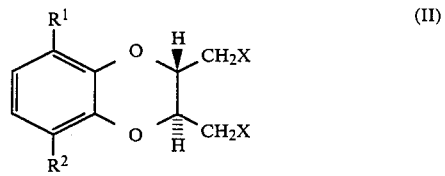

[where X is a leaving group such as a halogen atom, (e.g. chlorine, bromine or iodine), or a hydrocarbylsulphonyloxy group (e.g. methylsulphonyloxy)] with ammonia, aqueous ammonia or an amine of formula $RNH_2$ where R is as previously defined except that R is not a hydrogen atom or the group —CHO.

In a particular embodiment of this process, following the amination reaction, the resulting compound of general formula (I) or a salt thereof, may be converted into another compound of general formula (I). Thus, for example, when R is arylmethyl, the amination reaction may optionally be followed by removal of the arylmethyl group to yield a compound of formula (I) where R is a hydrogen atom.

The amination reaction is conveniently effected at an elevated temperature e.g. under reflux or in a sealed tube at e.g. 110° C., preferably in the presence of a suitable base e.g. sodium hydride or an alkali metal hydroxide such as sodium hydroxide, or in the presence of an excess of the amine $RNH_2$ optionally in the presence of a solvent such as a chlorinated hydrocarbon e.g. chloroform or an ether e.g. dioxan, or an alcohol eg ethanol. Optional removal of an arylmethyl group may be carried out, for example, by hydrogenolysis or, where appropriate, under acidic conditions, as described below.

According to another example (B), a compound of general formula (I) where R represents a hydrogen atom may be prepared by deprotection of a corresponding compound where R represents a protecting group. Suitable protecting groups include, for example, arylmethyl and acyl groups. Conventional deprotection procedures may be used. For example, where appropriate an arylmethyl group (e.g. benzyl) may be removed by hydrogenolysis using, for example, hydrogen in the presence of a catalyst, such as platinum or palladium on a support (e.g. charcoal), in a solvent such as an alcohol e.g. methanol. Alternatively, where appropriate, an arylmethyl group (e.g. trityl or bis (4-methoxyphenyl) methyl) may be removed under acidic conditions, using for example an acid such as trifluoroacetic acid, formic acid, hydrochloric acid or hydrobromic acid. Acyl groups may be removed by hydrolysis using an acid such as a mineral acid or a base such as an alkali metal hydroxide as appropriate. The protected starting materials for this process may be prepared using standard methods for the protection of amines, for example as described by McOmie (see above).

According to a further example (C), a compound of general formula (I) where R represents an alkyl group may be prepared by reduction of the corresponding compound in which R is an acyl group using a reducing agent such as lithium aluminium hydride or diborane in a suitable solvent such as ether or tetrahydrofuran at an elevated temperature e.g. reflux. Suitable acyl groups are, for example, formyl, acetyl, or carbonyloxyalkyl e.g. carbonyloxymethyl. The intermediate starting materials for this reaction may be prepared by acylation using conventional methods, for example by reaction of the compound of formula (I) in which R represents a hydrogen atom, with an acid chloride, acid anhydride, or ester.

Compounds of formula (I) in which $R_1$ and/or $R_2$ is cyano may be prepared by heating the corresponding carboxamide with a dehydrating agent such as phosphorus pentoxide ($P_2O_5$). The carboxamide may be prepared by methods analogous to those described herein for the preparation of a compound of formula (I).

The product of any of the processes (A), (B) and (C) described above may be subjected to one or two further reactions comprising:

(D)(i) converting the resulting compound of general formula (I) or a salt thereof into another compound of general formula (I); and/or (D)(ii) converting a compound of general formula (I) or a salt thereof into a physiologically acceptable salt thereof.

Thus, it is possible to prepare a compound of general formula (I) by a process comprising interconversion of another compound of general formula (I).

For example, a compound of general formula (I) in which R is a hydrogen atom may be converted by alkylation to a compound of general formula (I) in which R is an alkyl, substituted alkyl, alkenyl, alkynyl or aralkyl group. Conventional alkylation procedures may be used, for example reductive alkylation using an appropriate aldehyde with a complex metal hydride such as sodium or potassium borohydride or sodium cyanoborohydride in a suitable solvent such as an alcohol e.g. methanol. Methylation may be achieved using a formic acid/formaldehyde reagent system. Alternatively, the alkylation may be performed with an alkylating agent RX (where R is an alkyl, substituted alkyl, alkenyl, alkynyl or aralkyl group and X is a leaving group such as a halogen atom e.g. chlorine or bromine, or a hydrocarbylsulphonyloxy group e.g. p-toluenesulphonyloxy) preferably in the presence of a base, such as potassium carbonate, optionally in a solvent such as an alcohol, e.g. ethanol.

Another example of this embodiment is the preparation of a compound of general formula (I) where R is a group —CHO, which may be prepared by formylation of a corresponding compound of formula (I) in which R is a hydrogen atom using an appropriate formylating agent such as a formyl ester, e.g. an alkyl formate such as methyl formate.

In a further example, a compound of formula (I) in which $R^1$ and/or $R^2$ is an amino group may be prepared by reduction of a corresponding compound of formula (I) in which $R^1$ and/or $R^2$ is a nitro group. Suitable reducing agents include lithium aluminium hydride, in a solvent such as ether or tetrahydrofuran at elevated temperature, or hydrogen in the presence of a catalyst such as platinum or palladium on a support (e.g. charcoal) in a solvent such as an alcohol e.g. methanol.

In yet another example, a compound of formula (I) in which $R^1$ and/or $R^2$ is hydroxyl may be prepared by O-dealkylation of a corresponding compound of formula (I) in which $R^1$ and/or $R^2$ is an alkoxy group. For example, O-demethylation may be effected using an appropriate thiol e.g. methyl, ethyl or propyl mercaptan in the presence of a strong alkali metal base such as sodium hydride. The reaction is conveniently carried out in a refluxing solvent (e.g. dimethylacetamide, dimethylsulphoxide or dimethylformamide). Alternatively, the O-dealkylation reaction may be carried out using a Lewis acid such as boron tribromide or boron trichloride in a halohydrocarbon solvent (e.g. dichloromethane) or using pyridinium hydrochloride or hydrobromide as a melt, or aqueous hydrogen bromide.

Physiologically acceptable salts of the compounds of general formula (I) may be prepared by reacting the free base of formula (I) or a salt thereof with an appropriate acid, such as hydrogen chloride in the presence of a suitable solvent e.g. ethyl acetate, ether or $CH_2Cl_2$ or hydrochloric acid in a solvent such as methanol, to obtain the desired physiologically acceptable salt.

It may be desirable to protect various reactive substituents in the starting materials for a particular reaction or sequence of reactions and subsequently to remove the protecting group after completion of the reaction or sequence. Such protection and subsequent deprotection may be particularly pertinent when $R_1$ and/or when $R_2$ is a hydroxy or amino substituent. Conventional protection and deprotection procedures can be employed cf. "Protective Groups in Organic Chemistry" Ed. by J F W McOmie (Plenum Press, 1973). Thus, for example, a primary amine may be protected by formation of a phthalimide group which may subsequently be cleaved by treatment with a hydrazine, e.g. hydrazine hydrate or a primary amine, for example methylamine, and a phenolic hydroxyl group may be protected as an ether e.g. a 2-tetrahydropyranyl or methyl ether, which may subsequently be cleaved by a Lewis acid such as boron tribromide or aqueous hydrogen bromide.

The intermediate compounds of general formula (II) may be prepared by reaction of a corresponding diol of formula (III)

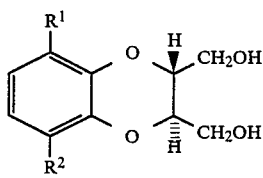
(III)

with a halide of formula $X_1A$ (where $X_1$ is a hydrocarbylsulphonyl group e.g. methylsulphonyl and A is a halogen atom e.g. a chlorine atom) in the presence of a base e.g. triethylamine in a solvent such as dichloromethane; or with a halogenating agent such as thionyl chloride, phosphorous tribromide or hydrogen iodide.

A diol (III) may be prepared by reduction of a corresponding dibenzyl ether of formula (IV):

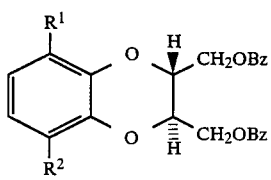
(IV)

(where Bz represents benzyl) using hydrogen and palladium on charcoal with a solvent e.g. ethanol.

Alternatively, an ether of formula (IV) may be treated with a Lewis acid, such as aluminium chloride, in a solvent such as toluene to yield a diol of formula (III).

A compound of formula (IV) may be prepared by heating the bis-tosylate (V):

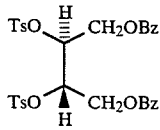
(V)

(where Ts represents

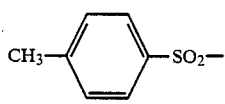

with a catechol of formula (VI)

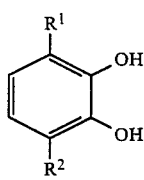
(VI)

in acetonitrile or dimethylformamide containing cesium fluoride or cesium carbonate.

The intermediates of formula (VI) are known compounds and may be prepared by standard methods of benzene ring substitution (cf. for example Barton, Linnell & Senior, Quat. J. Pharmacy & Pharmac., 1945, 18, 41–47 and Ladd & Weinstock, J. Org. Chem. 1981, 46, 203–206).

The bis-tosylate of formula (V) may be prepared by reaction of the known dibenzyl threitol of formula (VII)

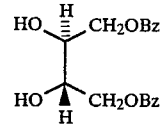
(VII)

with 4-toluenesulphonyl chloride in pyridine.

To obtain a specific enantiomer of formula (I), a diol of formula (III) having the required chirality should be used in the above processes. The enantiomeric diol starting material can be prepared from the appropriate dibenzyl threitol of formula (VII) or (VIII)

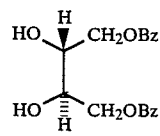
(VIII)

as described above.

A specific enantiomer of general formula (I) may also be prepared by resolution of a mixture of enantiomers of formula (I) by conventional methods, e.g. by salt formation with an optically active acid followed by separation of the resulting diastereoisomeric salts, e.g. by fractional crystallisation. Alternatively, resolution may be effected at any suitable intermediate stage.

The following examples illustrate the invention. All temperatures are in °C. In the following, ER represents ether, IMS represents industrial methylated spirits, MeOH represents methanol, EtOH represents ethanol and "light petroleum" refers to the fraction boiling at 60°–80°. "Dried" refers to drying over magnesium sulphate unless otherwise stated.

INTERMEDIATE 1

(±)-(trans)-5-Fluoro-2,3-dihydro-2,3-bis[(phenylmethoxy)methyl]-1,4-benzodioxin

A mixture of 3-fluorobenzene-1,2-diol (5.12 g) and (R*,R*)-(±)-1,4-bis(phenylmethoxy)-2,3-butanediol, bis(4-methylbenzenesulphonate) (24.4 g) was stirred with dimethylformamide (D.M.F.) (160 ml) under a nitrogen stream for 45 min. Anhydrous cesium carbonate (13.0 g) was added and the mixture was heated to 150° under reflux for 18 hours. The dark brown mixture was cooled to 30° and diluted with di-isopropyl ether (370 ml) and water (320 ml). The layers were separated and the aqueous layer was re-extracted with di-isopropyl ether (150 ml then 100 ml). The extracts were sequentially washed with M hydrochloric acid (300 ml), 30% aqueous sodium chloride (100 ml) and were combined and evaporated in vacuo to a dark brown oil (12.6 g) which was dissolved in light petroleum-dichloromethane (3:1) (40 ml) and chromatographed over Sorbsil (126 g) using light petroleum-dichloromethane mixtures of gradually increasing polarity. Combination of appropriate fractions and evaporation of the solvents gave the title compound as a yellow oil (7.0 g), NMR $\tau$ (CDCl$_3$) 2.6–2.8 (10H, m, Ph), 3.18–3.38 (3H, m, 6-H, 7-H, 8-H), 5.32–5.58 (4H, m, CH$_2$Ph), 5.64 (2H, m, 2-H, 3-H), 6.06–6.32 (4H, m, CH$_2$O).

Intermediates 2–8 (shown in Table 1) were prepared in a similar manner from the appropriate catechol and (R*,R*)-(±)-1,4-bis(phenylmethoxy)-2,3-butanediol, bis(4-methylbenzenesulphonate).

TABLE 1

| R | R' | Reaction Solvent | NMR τ (CDCl₃) | | | | | | |
|---|---|---|---|---|---|---|---|---|---|
| | | | Ph | Ph CH₂ | OCH₃ | 2-H,3-H | Aromatic | Me | OMe |
| CH₃ (2) | H | CH₃CN | 2.68 | 5.41 | 6.21 | 5.6–5.8 | 3.29 | 7.78 | — |
| CH₃O (3) | H | CH₃CN | 2.7 | 5.2–5.8 | 5.8–6.5 | 5.2–5.8 | 3.0–3.6 | — | 6.13 |
| Cl (4) | H | CH₃CN | 2.66 | 5.3–5.55 | 6.0–6.3 | 5.55–5.7 | 3.0–3.3 | — | — |
| NO₂ (5) | H | D.M.F. | 2.6–2.8 | 5.3–5.54 | 6.05–6.27 | 5.6 | 2.51,2.85 3.12 | — | — |
| CH₃ (6) | CH₃ | CH₃CN | 2.6–2.8 | 5.38–5.44 | 6.1–6.3 | 5.67 | 3.39 | 7.82 | — |
| Cl (7) | Cl | CH₃CN | 2.73 | 5.43 | 6.18 | 5.6 | 3.17 | — | — |
| F (8) | F | D.M.F. | 2.5–2.8 | 5.37,5.48 | 6.1,6.2 | 5.58 | 3.39 | — | — |

INTERMEDIATE 9

(±)-(trans)-5-Chloro-2,3-dihydro-1,4-benzodioxin-2,3-dimethanol

A solution of (trans)-(±)-5-chloro-2,3-bis[(phenylmethoxy)methyl]-2,3-dihydro-1,4-benzodioxin (2.2 g) in trifluoroacetic acid (T.F.A.) (50 mls) was hydrogenated over 10% palladium on carbon (0.22 g). The solid was filtered off, washed with chloroform and the solution was evaporated to dryness to give the diol as a colourless liquid 1.2 g, NMR τ (CDCl₃) 2.9–3.3 (3H, m, aromatic), 7.72 (2H, s, OH), 5.7–6.2 (6H, m, 2-H, 3-H, CH₂O).

Intermediate 11–15 (shown in Table 2) were prepared in a similar manner.

Intermediate 11 from Intermediate 2 diluted with ethyl acetate (75 ml) and the layers were separated. The aqueous (lower) layer was re-extracted with ethyl acetate (2×50 ml) and the organic solutions were washed with 30% aqueous sodium chloride (25 ml) and were combined and concentrated in vacuo to 36 g, giving a thick slurry of slightly purple crystals. After 30 min. at 20°, the crystals were harvested, washed with toluene (10 ml), light petroleum (20 ml) and di-isopropyl ether (20 ml) and dried to give the title compound (2.93 g) m.p. 122°–124°. Concentration of the mother liquor gave a crude second crop of title compound (0.32 g) which after chromatographic purification afforded a further quantity of pure title compound (0.24 g) m.p. 121°–123°. NMR τ (DMSO-d₆) 3.1–3.3 (3H, m, aromatic), 4.85–5.0 (2H, m, OH), 5.8–5.9 (2H, m, 2-H, 3-H), 6.1–6.4 (4H, m, CH₂O).

Intermediate 16 (shown in table 2) was prepared in a similar manner from intermediate 5.

TABLE 2

| R | R' | Reaction Solvent | NMR (τ) | | | | | | |
|---|---|---|---|---|---|---|---|---|---|
| | | | Solvent | Aromatic | CH₂OH | 2-H,3-H | OH | Me | M.pt |
| CH₃ (11) | H | EtOH | CDCl₃ | 3.3 | 5.8–6.1 | 5.8–6.1 | 7.59 | 7.8 | — |
| CH₃O (12) | H | EtOH | compound unstable, used without characterisation | | | | | | |
| CH₃ (13) | CH₃ | MeOH | DMSO-d₆ | 3.42 | 6.3 | 5.9 | 5.04 | 7.89 | 77–9° |
| Cl (14) | Cl | TFA | DMSO-d₆ | 3.02 | 6.0–6.4 | 5.75 | 4.8–5.5 | — | 172–5° |
| F (15) | F | EtOH | DMSO-d₆ | 3.2 | 6.08–6.32 | 5.8 | 4.89 | — | 128–130° |
| NO₂ (lb) | H | Toluene | used without characterisation | | | | | | |

Intermediate 12 from Intermediate 3
Intermediate 13 from Intermediate 6
Intermediate 14 from Intermediate 7
Intermediate 15 from Intermediate 8

INTERMEDIATE 10

(±)-(trans)-5-Fluoro-2,3-dihydro-1,4-benzodioxin-2,3-dimethanol

Intermediate 1 (7.0 g) was dissolved in a mixture of toluene (70 ml) and anisole (7.8 ml) and the solution was stirred and cooled to −5° under a gentle stream of nitrogen. Anhydrous aluminium chloride (2.4 g) was added and the temperature was maintained at 0°–5° for 20 min. More anhydrous aluminium chloride (2.4 g) was added and after 20 min. at 0°–5° the mixture was allowed to warm to 20° with continued stirring. After 20 min. at 20°, it was cooled back to 0°, water (25 ml) was added and after 5 min. stirring at 20°, the mixture was

INTERMEDIATE 17

(±)-(trans)-5-Fluoro-2,3-dihydro-1,4-benzodioxin-2,3-dimethanol, bis methanesulphonate A solution of Intermediate 10 (3.10 g) in dichloromethane (30 ml) and triethylamine (6.4 ml) was stirred for 10 min, with ice-bath cooling. A solution of methanesulphonyl chloride (3.2 ml) in dichloromethane (10 ml) was added during 10 min. and the resultant suspension was stirred for 30 min. Water (25 ml) was added and the mixture was stirred for 20 min, the layers were then separated and the aqueous layer was re-extracted with dichloromethane (25 ml). The organic solutions were washed with water (25 ml), and were combined and evaporated to an oil which was chromatographed over Sorbsil (40 g), eluting with 9:1 dichloro methane-ethyl acetate. Appropriate fractions were combined and evaporated to a pale yellow oil (5.9 g) which crystallised slowly from ethyl acetate-di-isopropyl ether to afford the title compound as prisms (4.15 g) m.p. 65.5°–67.5°. NMR τ (CDCl$_3$) 3.1–3.34 (3H, m, aromatic), 5.3–5.5 (4H, m, CH$_2$O) 5.5–5.65 (2H, m, 2-H, 3-H) 6.89, 6.91 (6H, singlets, CH$_3$SO$_3$).

Intermediates 18–24 (shown in Table 3) were prepared in a similar manner

Intermediate 18 from Intermediate 11
Intermediate 19 from Intermediate 12
Intermediate 20 from Intermediate 9
Intermediate 21 from Intermediate 16
Intermediate 22 from Intermediate 13
Intermediate 23 from Intermediate 14 liquor gave a third crop (0.6 g). A recrystallised sample, m.p. 80°–81° had the following analysis: Found: C, 71.7; H, 5.65; N, 4.95; F, 6.8 C$_{17}$H$_{16}$FNO$_2$ requires: C, 71.6; H, 5.65; N, 4.9; F, 6.65% NMR τ (CDCl$_3$) 2.6–2.8 (5H, broad singlet, Ph), 3.1–3.35 (3H, m, aromatics), 5.6–5.8 (2H, m, 3a-H, 9a-H), 6.09 and 6.19 (2H, ABq, Ph CH$_2$), 6.65–6.85 and 6.9–7.1 (4H, multiplets, 1-H$_2$, 3-H$_2$). The compounds of Examples 2–7 were prepared in a similar manner to the compound of Example 1.

Example 2 from Intermediate 18
Example 3 from Intermediate 19
Example 4 from Intermediate 20
Example 5 from Intermediate 22
Example 6 from Intermediate 23
Example 7 from Intermediate 24

TABLE 4

| R | R' | Salt or free base | Solvent | NMR τ Aromatic | Ph | Ph CH$_2$ | 3a-H,9a-H | 1-H$_2$,3-H$_2$ | NH$^+$ | Me | OMe | M.pt |
|---|---|---|---|---|---|---|---|---|---|---|---|---|
| CH$_3$ (2) | H | HCl | TFA | 3.17 | 2.47 | 5.34 | 5.2–6.7 | 5.2–6.7 | 0.75 | 7.79 | — | — |
| CH$_3$O (3) | H | HCl | TFA | 2.7–3.4 | 2.43 | 5.31 | 5.2–5.7 | 5.7–6.7 | 0.75 | — | 6.0 | — |
| Cl (4) | H | HCl | TFA | 2.8–3.2 | 2.3–2.6 | 5.2,5.5 | 5.4–6.1 6.3–6.5 | 5.4–6.1 6.3–6.5 | — | — | — | 215–222° |
| CH$_3$ (5) | CH$_3$ | Free base | CDCl$_3$ | 3.36 | 2.6–2.8 | 6.07,6.19 | 5.78 | 6.73,7.02 | — | 7.83 | — | 83° |
| Cl (6) | Cl | HCl | TFA | 2.94 | 2.39 | | 5.0–6.6 | | — | — | — | 250–257° |
| F (7) | F | Free base | CDCl$_3$ | 3.34 | 2.5–2.8 | 6.07,6.17 | 5.67 | 6.69,6.96 | — | — | — | 86° |

Intermediate 24 from Intermediate 15

TABLE 3

| R | R' | Solvent | NMR τ Aromatic | CH$_2$O | 2-H,3-H | MeSO$_3$ | Me | OMe | M.pt |
|---|---|---|---|---|---|---|---|---|---|
| CH$_3$ (18) | H | DMSO-d$_6$ | 3.19 | 5.2–5.7 | 5.2–5.7 | 6.69 | 7.8 | — | — |
| CH$_3$O (19) | H | CDCl$_3$ | 3.0–3.6 | 5.3–5.7 | 5.3–5.7 | 6.82 | — | 6.1 | — |
| Cl (20) | H | CDCl$_3$ | 2.92–3.2 | 5.3–5.5 | 5.5–5.7 | 6.87,6.91 | — | — | — |
| NO$_2$ (21) | H | DMSO-d$_6$ | 2.35, 2.58, 2.87 | 5.1–5.6 | 5.1–5.6 | 6.7 | — | — | 140–1° |
| CH$_3$ (22) | CH$_3$ | CDCl$_3$ | 3.34 | 5.46 | 5.6 | 6.93 | 7.85 | — | 121–3° |
| Cl (23) | Cl | CDCl$_3$ + DMSO-d$_6$ | 3.1 | 5.3–5.5 | 5.3–5.5 | 6.81 | — | — | 142–4° |
| F (24) | F | CDCl$_3$ | 3.33 | 5.38 | 5.54 | 6.89 | — | — | 106–7° |

EXAMPLE 1

(±)-(trans)-5-Fluoro-2,3,3a,9a-tetrahydro-2-(phenylmethyl)-1H-[1,4]benzodioxino[2,3-c]pyrrole A homogenised mixture of phenylmethanamine (8 ml) and Intermediate 17 (5.3 g) was heated to 130° for 15 min. then cooled to 25°. The partly crystalline mixture was partitioned between di-isopropyl ether (80 ml) and water (80 ml). The aqueous layer was re-extracted with di-isopropyl ether (100 ml) and the organic solutions were sequentially washed with 2.5% aqueous acetic acid (2×50 ml) and 15% aqueous sodium chloride (100 ml) containing sodium hydrogen carbonate (5 g). They were then combined and evaporated in vacuo to an orange-brown oil (3.8 g) which crystallised spontaneously. This was recrystallised from di-isopropyl ether—light petroleum (1:1) to give pink crystals of the title compound as two crops; (1) 1.5 g m.p. 79°–81° and (2) 1.4 m.p. 79.5°–81°. Chromatography of the mother

EXAMPLE 8

(±)-(trans)-5-Fluoro-2,3,3a,9a-tetrahydro-1H[1,4]benzodioxino[2,3-c]pyrrole hydrochloride A solution of the compound of Example 1 (2.3 g) in IMS (110 ml) was stirred under hydrogen at ca. 25° with 5% palladium on charcoal (1.15 g) until uptake ceased (270 ml). The catalyst was filtered off using a kieselguhr pad, the filter was washed through with IMS (3×20 ml) and the combined filtrates were evaporated in vacuo to a pale pink oil (1.6 g). This was re-dissolved in IMS (10 ml) and 10M hydrochloric acid (1 ml) was added. After 30 min. at 20°, the resultant white crystals were harvested, washed with IMS (3 ml), 1:1 IMS-di-isopropyl ether (4 ml) and di-isopropyl ether (2×5 ml) to afford the title compound as a hemihydrate, (1.09 g) m.p. ca. 245° (sublimes above 210°) NMR τ (DMSO-d$_6$) −0.25 (2H, broad s, NH$_2$$^+$), 2.9–3.2 (3H, m, 6-H, 7-H and 8-H), 5.4–5.65 (2H, m, 3a-H, 9a-H), 6.0–6.3, 6.6–6.8 (4H, ABq, 1-H₂, 3-H₂).

The compounds of Examples 9–14 were prepared in a similar manner to the compound of Example 8 from the compounds of Examples 2–7.

TABLE 5

| R | R' | Solvent | NMR τ Aromatic | 3a-H, 9a-H | 1-H₂, 3-H₂ | NH₂⁺ | Me | OMe | M.pt |
|---|---|---|---|---|---|---|---|---|---|
| CH₃ (9) | H | DMSO-d₆ | 3.22 | 5.5, 5.9 | 6.1–6.4, 6.6–7.0 | 0.0 | 7.87 | — | 258–264° |
| CH₃O (10) | H | TFA | 2.8–3.4 | 5.3, 5.6 | 5.6–6.6 | 1.86 | — | 5.97 | 241–244° |
| Cl (11) | H | DMSO-d₆ | 2.81,2.9, 3.1 | 5.4–5.65 | 6.0–6.3, 6.5–6.8 | −0.19 | — | — | 275–277° |
| CH₃ (12) | CH₃ | DMSO-d₆ | 3.24 | 5.66 | 6.1–6.25, 6.5–6.8 | −0.1 | 7.83 | — | 250° |
| Cl (13) | Cl | DMSO-d₆ | 2.77 | 5.42 | 6.09,6.62 | −0.19 | — | — | 270° (dec.) |
| F (14) | F | DMSO-d₆ | 3.01 | 5.45 | 6.13,6.65 | −0.36 | — | — | 77–9° |

EXAMPLE 9

(±)-(trans)-2,3,3a,9a-Tetrahydro-5-methyl-1H-[1,4]benzodioxino[2,3-c]pyrrole hydrochloride.

EXAMPLE 10

(±)-(trans)-2,3,3a,9a-Tetrahydro-5-methoxy-1H-[1,4]benzodioxino[2,3-c]pyrrole hydrochloride.

EXAMPLE 11

(±)-(trans)-5-Chloro-2,3,3a,9a-tetrahydro-1H-[1,4]benzodioxino[2,3-c]pyrrole hydrochloride.

EXAMPLE 12

(±)-(trans)-2,3,3a,9a-Tetrahydro-5,8-dimethyl-1H-[1,4]benzodioxino[2,3-c]pyrrole hydrochloride.

EXAMPLE 13

(±)-(trans)-5,8-Dichloro-2,3,3a,9a-tetrahydro-1H-[1,4]benzodioxino[2,3-c]pyrrole hydrochloride.

EXAMPLE 14

(±)-(trans)-5,8-Difluoro-2,3,3a,9a-tetrahydro-1H-[1,4]benzodioxino[2,3-c]pyrrole hydrochloride.

EXAMPLE 15

(±)-(trans)-2,3,3a,9a-Tetrahydro-5-nitro-1H-[1,4]-benzodioxino[2,3-c]pyrrole hydrochloride (a)

(±)-(trans)-2-[bis(4-methoxyphenyl)methyl]-2,3,3a,9a-Tetrahydro-5-nitro-1H-[1,4]benzodioxino[2,3-c]pyrrole A solution of Intermediate 21 (2.0 g) and [bis(4-methoxyphenyl)]methanamine (3.7 g) in 1,4-dioxan (10 ml) was heated at ca. 90° for 65 hr. under nitrogen. The mixture, which had partially crystallised, was cooled to 25° and diluted with ethyl acetate (30 ml). The crystals were filtered off and washed with ethyl acetate (3×10 ml). The combined filtrates were washed with 3% aqueous sodium chloride (60 ml) containing glacial acetic acid (2 ml), then with saturated aqueous sodium bicarbonate (50 ml). The washes were re-extracted with ethyl acetate (25 ml). The combined extracts were evaporated to a pale yellow oil (4.6 g). This was chromatographed over Sorbsil (30 g) eluting with di-isopropyl ether, then ethyl acetate to give impure title compound (2.1 g). This was rechromatographed over Sorbsil (40 g) eluting with 5:1 di-isopropyl ether-dichloromethane to give pure title compound, crystallised from di-isopropyl ether as two crops (1.23 g; m.p. 139°–140.5° and 0.47 g; m.p. 136°–139°).

(b)

(±)-(trans)-2,3,3a,9a-Tetrahydro-5-nitro-1H-[1,4]-benzodioxino[2,3-c]pyrrole hydrochloride A solution of (±)-(trans)-2-[bis(4-methoxyphenyl)methyl]-2,3,3a,9a-tetrahydro-5-nitro-1H-[1,4]benzodioxino[2,3-c]pyrrole (1.12 g) in formic acid (10 ml) was heated under reflux with 10M hydrochloric acid (0.5 ml), water (1 ml) and chloroform (5 ml) for 70 minutes. The maroon mixture was cooled and partitioned between chloroform (20 ml) and water (10 ml). The chloroform layer was re-extracted with water (10 ml) and the aqueous solutions were sequentially washed with chloroform (20 ml), combined and evaporated to ca. 2 ml, when crystals formed. These were triturated with warm propan-1-ol (5 ml), cooled to 20° for 1 hour and harvested to give a first crop of the title compound (0.58 g). Concentration of the mother liquor gave a small second crop (0.03 g). Recrystallisation of the first crop from slightly aqueous propan-1-ol gave purer title compound (0.54 g) m.p. ca. 280° (dec.).

EXAMPLE 16

(±)-(trans)-2,3,3a,9a-Tetrahydro-2-(phenylmethyl)-1H-[1,4]benzodioxino[2,3-c]pyrrole-5-carbonitrile (a)

(±)-(trans)-2,3-Dihydro-2,3-bis[(phenylmethoxy)methyl]-1,4-benzodioxin-5-carboxylic acid, benzenemethanamine (salt) (Compound A)

A mixture of methyl 2,3-dihydroxybenzoate (30 g), cesium carbonate (58.1 g) and (R*,R*)-(±)-1,4-bis(-phenylmethoxy)-2,3-butanediol, bis(4-methylbenzenesulphonate) (106.3 g) in acetonitrile (1400 ml) was stirred and heated under reflux for 5 days, during the first 2 hours of which ca. 80 ml acetonitrile was removed to effect azeotropic drying. The solid was filtered off from the cooled mixture and the filtrate was evaporated to dryness and the residue was suspended in diethyl ether and water added. A dark, sticky residue was discarded and the aqueous layer was back extracted with ether. The combined ether layers were extracted with cold 2M sodium hydroxide solution, and brine, dried over magnesium sulphate and the solvent was evaporated. The resulting oil (65.3 g) was heated at reflux in water (300 ml) containing potassium hydroxide (30 g) for 2 hours, cooled and diluted with dichloromethane. The organic layer was washed with 2M hydrochloric acid, 30% brine dried over magnesium sulphate and evaporated to an oil (61 g) which was taken up in diethyl ether (ca. 150 ml). To this stirred solution was added benzylamine (7.5 ml) and after overnight chilling the precipitated solid was collected, washed with ether and dried to give the title compound as an off-white solid 38.2 g, NMR τ (DMSO-d$_6$) 2.0–3.4 (21H, m, aromatic, and NH$_3^+$), 5.2–6.6 (12H, multiplets, benzyl CH$_2$, 2-H, 3-H, and CH$_2$O).

(b)
(±)-(trans)-2,3-Dihydro-2,3-bis(hydroxymethyl)-1,4-benzodioxin-5-carboxylic acid (Compound B)

A solution of Compound A (36.93 g) in ether (500 ml) was extracted twice with 2M hydrochloric acid (400 ml, 100 ml) and the aqueous layers back extacted with ether (50 ml). The combined ether layers were washed with 30% sodium chloride solution and the solvent removed to afford an oil (32 g) which was taken up in IMS (350 ml). This solution was hydrogenated at 45° in the presence of 5% palladium on carbon (16 g) until uptake was complete. The catalyst was removed by filtration, washed with IMS and the filtrate was evaporated to dryness. The product was crystallised from ethyl acetate to give the title compound as a white solid 14.5 g (two crops) m.pt. 123°–5°.

(c)
(±)-(trans)-2,3-Dihydro-2,3-bis[[(methylsulphonyl)oxy]methyl]-1,4-benzodioxin-5-carboxylic acid, anhydride (Compound C)

Triethyamine (34.8 ml) was added to a stirred, chilled solution of Compound B (17.04 g) in methylene chloride (300 ml). At 0° to −5° a solution of methanesulphonyl chloride (13 ml) in methylene chloride (50 ml) was added over approx. 5 minutes. After 1 hour, when the temperature had risen to ambient, water was added and the layers were separated. The organic layer was washed twice with 2M hydrochloric acid solution and the aqueous layers back extracted with methylene chloride. The combined organic extracts were washed with brine, dried over magnesium sulphate, stirred with decolourising charcoal (1 g) and evaporated to dryness to give the title compound as a white foam. 24.1 g, NMR τ (CDCl$_3$) 2.40, 2.82 and 3.05 (3H, multiplets, aromatic), 5.1 to 5.9 (6H, br, 2-H, 3-H and CH$_2$O), 6.92 and 6.96 (each 3H, s, CH$_3$SO$_3$).

(d)
(±)-(trans)-2,3-Dihydro-2,3-bis[[(methylsulphonyl)oxy]methyl]-1,4-benzodioxin-5-carboxamide (Compound D)

A solution of Compound C (18.0 g) in ethyl acetate (150 ml) was stirred at room temperature and ammonia solution (SG 0.88; 4.5 ml) was added. After 10 minutes water (150 ml) was let in and the layers were separated. The aqueous layer was back extracted with ethyl acetate and the combined organic layers were washed with aqueous sodium bicarbonate solution, dried over magnesium sulphate and evaporated to a semi-solid residue. Crystallisation from ethyl acetate (ca. 50 ml) gave the title compound as buff coloured dense solid 7.12 g m.pt 144°–146°.

(e)
(±)-(trans)-2,3-3a,9a-Tetrahydro-2-(phenylmethyl)-1H-[1,4]benzodioxino[2,3-c]pyrrole-5-carboxamide (Compound E)

A solution of Compound D (6.76 g) in benzylamine (10 ml) was heated to 120° for 10 minutes. The warm (85°) solution was poured into stirred, distilled water (300 ml) at room temperature. An oil deposited which quickly solidified. After 1 hour's brisk stirring, the buff coloured particulate solid was collected, washed with water and dried to give the title compound 5.03 g, m.pt 155°–165°.

(f)
(±)-(trans)-2,3,3a,9a-tetrahydro-2-(phenylmethyl)-1H-[1,4]benzodioxino[2,3-c]pyrrole-5-carbonitrile An intimate mixture of Compound E (1.24 g) and phosphorus pentoxide (0.6 g) was heated to 165°. Two further aliquots of phosporus pentoxide (0.6 g each) were added at 10 minute intervals, mixing well in, while maintaining the temperature in the range 165° to 180°. Ten minutes after the final addition the solid mass was triturated with aqueous potassium hydroxide, ethyl acetate mixture and stirred well until free of solid. Evaporation of the organic layer gave a brown oil which was chromatographed on silica gel (50 g). Elution with ethyl acetate:petrol b.pt. 60°–80° (1:1) gave an oil (0.8 g) which solidified on trituration, with petrol, b.pt. 60°–80°. The product was collected, washed with petrol and dried to give the title compound as a buff coloured solid (0.57 g) m.pt. 101°–103°, NMR τ (CDCl$_3$) 2.74 (5H, s, Ph), 2.5–3.4 (3H, m, aromatic), 5.4–6.1 (2H, m, 3a-H, 9a-H), 6.18 (2H, s, CH$_2$ Ph), 6.5–7.4 (4H, m, 1-H$_2$, 3-H$_2$).

EXAMPLE 17

(±)-(trans)-2,3,3a,9a-tetrahydro-1H-[1,4]benzodioxino[2,3-c]pyrrole-5-carbonitrile, hydrochloride A solution of (±)-(trans)-2,3,3a,9a-tetrahydro-2-phenylmethyl-1H-[1,4]benzodioxino[2,3-c]pyrrole-5-carbonitrile (0.55 g) in IMS (30 ml) was hydrogenated over 10% palladium on charcoal (0.2 g). When uptake had ceased the catalyst was filtered off, washed with IMS and the filtrate was concentrated to ca. 20 ml volume. Conc. hydrochloric acid (5 drops) was added and a solid crystallised. After ageing 1 hour in the cold the product was collected, washed with IMS and dried to give the title compound as a white solid 0.25 g m.pt. 249°–254°, NMR τ (DMSO-d$_6$) 2.53 (1H, dd, J 8 and 2, 6-H), 2.60 (1H, dd, J 8 and 2, 8-H), 2.84 (1H, t, J 8, 7-H), 5.44 (2H, m, 3a-H, 9a-H), 6.0–6.3 and 6.4–7.0 (4H, multiplets, 1-H$_2$, 3-H$_2$).

EXAMPLE 18

(±)-(trans)-2,3-3a,9a-Tetrahydro-1H[1,4]benzodioxino[2,3-c]pyrrole-5-ol hydrochloride A solution of (±)-(trans)-2,3,3a,9a-tetrahydro-5-methoxy-1H-[1,4]benzodioxino[2,3-c]pyrrole (0.11 g) in 48% hydrobromic acid (5 mls) was heated at 100° for 4.5 hours. The resulting solution was evaporated to dryness, sodium carbonate solution was added, the mixture was saturated with salt and extracted with ethyl acetate for 20 hours in a continuous extraction apparatus. The organic solution was evaporated to dryness and the crude product was purified by preparative TLC on silica gel. The required component was eluted with hot methanol, the solvent was evaporated and the residue was dissolved in 2M hydrochloric acid. Evaporation of the solvent and crystallisation of the resulting solid from 2M hydrochloric acid gave the title compound (35 mg). NMR τ (DMSO-d$_6$) −0.22 (2H, s, NH$_2^+$), 0.46 (1H, s, OH), 3.26 (1H, t, J 8 Hz, 7H), 3.41 (1H, dd, J 8, 2 Hz, 8H), 3.51 (1H, dd, J 8, 2 Hz, 6H), 5.5–5.8 (2H, m, 3a-H, 9a-H), 6.1–6.3, 6.6–6.8 (4H, multiplets, 1-H$_2$, 3-H$_2$).

EXAMPLE 19

(±)-(trans)-5-Fluoro-2,3,3a,9a-tetrahydro-2-methyl-1H-[1,4]benzodioxino[2,3,c]pyrrole hydrochloride A solution of (±)-(trans)-5-fluoro-2,3,3a,9a-tetrahydro-1H-[1,4]benzodioxino[2,3-c]pyrrole hydrochloride in water (10 ml) was basified with 50% sodium hydroxide and extracted with ethyl acetate (1×20 ml, 1×10 ml and 1×5 ml). The combined extracts were evaporated in vacuo to an oil, redissolved in dichloromethane (25 ml) and decanted to remove some solid material. Evaporation of the solvent in vacuo gave a solid (0.52 g) m.pt. 92°, which was heated for 2 hours on a steam bath with a mixture of water (5 ml), 98% formic acid (0.5 ml), and 40% formaldehyde solution (1.12 ml). The clear solution was diluted with water (20 ml), basified with 50% sodium hydroxide and extracted with dichloromethane (3×10 ml). The combined extracts were evaporated to give the free base of the title compound as a solid (0.55 g), m.pt. 78°–9°. The free base was dissolved in hot IMS (10 ml) and concentrated hydrochloric acid (0.3 ml) was added and the solution was evaporated to leave a solid. The solid was redissolved in IMS (10 ml) and the solvent evaporated in vacuo to give a solid (0.65 g) m.pt. 263°–5° (dec.). Recrystallisation from IMS/ether gave the title compound, m.p. 260°–2° (dec.) NMR τ (DMSO-d$_6$) 2.94–3.18 (3H, m, aromatic), 5.41 (2H, br, 3a-H, 9a-H), 5.9–6.6 (4H, multiplets, 1-H$_2$, 3-H$_2$), 7.02 (3H, s, NCH$_3$).

PHARMACEUTICAL EXAMPLES

In the following examples, 'Active Ingredient' refers to (±)trans-5-fluoro-2,3,3a,9a-tetrahydro-1H-[1,4]-benzodioxino[2,3-c]pyrrole hydrochloride. Other compounds of the invention may be formulated in similar fashion.

| 1. Oral Capsule | per capsule |
| --- | --- |
| Active Ingredient | 50 mg |
| Magnesium stearate | 0.5 mg |
| Anhydrous lactose | 50 mg |

Blend the active ingredient with the lactose and magnesium stearate. Fill the blend into appropriate size hard gelatin capsules (lock fitting type) on an automatic capsule filling machine).

| 2. Oral Syrup | per 5 ml dose |
| --- | --- |
| Active Ingredient | 50 mg |
| Sodium citrate | 25 mg |
| Citric acid | to pH 4.5 |
| Sunset yellow FCF (Dye) | 0.25 mg |
| Methyl hydroxybenzoate sodium | 5.0 mg |
| Propyl hydroxybenzoate sodium | 2.0 mg |
| Liquid orange flavour | qS |
| Sucrose | 3.25 g |
| Purified water | to 5.0 ml |

Dissolve the sucrose in a minimum quantity of water. Add a concentrated solution of sodium citrate with stirring and adjust the pH to 4.5 with citric acid. With continued stirring, add a 10% aqueous solution of the active ingredient, followed by a solution of the dye, a solution of the hydroxybenzoates and lastly the flavour. Adjust almost to volume with water and stir. Check the pH and adjust to 4.5 with citric acid if necessary. Make up to volume with water.

| 3. Oral Tablet | per tablet |
| --- | --- |
| Active Ingredient | 50 mg |
| Polyvinylpyrrolidone | 4.0 mg |
| Sodium starch glycollate | 10.0 mg |
| Magnesium stearate | 2.0 mg |
| Lactose to tablet core weight to | 200 mg |

Blend the active ingredient with the lactose. Add a sufficient quantity of polyvinylpyrrolidone solution to produce a damp mass suitable for granulation. Prepare the granules and dry using a tray or fluid bed dryer. Pass through a sieve, blend with the remaining ingredients and compress into 8 mm diameter tablets on a tablet machine.

Film coat the tablet cores with hydroxypropyl methyl cellulose or similar film forming material, using either an aqueous or non-aqueous solvent system. A plasticizer and suitable colour may be included in the film coating solution.

We claim:

1. A compound of formula (I):

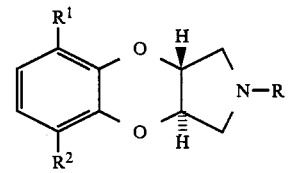

wherein

R is a hydrogen atom or a group selected from C$_{1-6}$ alkyl unsubstituted or substituted by C$_{3-7}$ cycloalkyl, C$_{3-6}$ alkenyl, C$_{3-6}$ alkynyl, C$_{3-7}$ cycloalkyl, phenalkyl in which the alkyl moiety contains 1–5 carbon atoms, and —CHO; R$^1$ is a group selected from halogen, C$_{1-4}$ alkyl, or hydroxyl; and R$^2$ is a hydrogen atom or a substituent as defined above for R$^1$;

and the physiologically acceptable salts thereof.

2. A compound according to claim 1, wherein, in the general formula (I), R is a hydrogen atom.

3. A compound according to claim 1, wherein, in the general formula (I), R is a C$_{1-3}$ alkyl group.

4. A compound according to claim 1, wherein, in the general formula (I), R$^1$ is a halogen atom or a C$_{1-4}$ alkyl group.

5. A compound according to claim 1, wherein, in the general formula (I), R$^2$ is a hydrogen or fluorine atom.

6. A compound according to claim 1, wherein, in the general formula (I), R is a hydrogen atom or a methyl or ethyl group; R$^1$ is a chlorine or fluorine atom or a methyl group; and R$^2$ is a hydrogen or fluorine atom.

7. A compound selected from (±)-trans-2,3,3a,9a-tetrahydro-5-methyl-1H-[1,4]benzodioxino[2,3-c]pyrrole, and its 3aS- and 3aR-isomers; (±)-trans-5-chloro-2,3,3a,9a-tetrahydro-1H-[1,4]benzodioxino[2,3-c]-pyrrole, and its 3aS- and 3aR-isomers; (±)-trans-5,8-difluoro-2,3,3a,9a-tetrahydro-1H-[1,4]benzodioxino[2,3-c]pyrrole and its 3aS- and 3aR-isomers; and their physiologically acceptable salts.

8. A compound selected from (±)-trans-5-fluoro-2,3,3a,9a-tetrahydro-1H-[1,4]benzodioxino[2,3-c]pyrrole and its 3aS- and 3aR-isomers and their physiologically acceptable salts.

9. (±)-trans-5-Fluoro-2,3,3a,9a-tetrahydro-1H-[1,4]benzodioxino[2,3-c]pyrrole hydrochloride and its 3aS- and 3aR-isomers.

10. An alpha$_2$-adrenoreceptor antagonist composition comprising a pharmaceutically effective amount of an alpha$_2$-adrenoreceptor antagonist compound selected from the group consisting of compounds of formula (I), claim 1, physiologically acceptable salts thereof and their mixtures, together with a physiologically acceptable carrier or excipient.

11. An alpha$_2$-adrenoreceptor composition according to claim 10 which also comprises an effective amount of an established antidepressant selected from the group consisting of desmethylimipramine, imipramine or amitriptyline.

12. A method of treating or preventing depression susceptible to amelioration by an alpha$_2$-adrenoreceptor antagonist comprising administering an effective amount of a compound selected from the group consisting of compounds of formula (I), claim 1, physiologically acceptable salts thereof and mixtures thereof.

13. A method of treating or preventing migraine and senile dementia susceptible to amelioration by an alpha$_2$-adrenoreceptor antagonist comprising administering an effective amount of a compound selected from the group consisting of compounds of formula (I), claim 1, physiologically acceptable salts thereof and mixtures thereof.

14. A method of treating or preventing thrombosis, diabetes and hypertension susceptible to amelioration by an alpha$_2$-adrenoreceptor antagonist comprising administering an effective amount of a compound selected from the group consisting of compounds of formula (I), claim 1, physiologically acceptable salts thereof and mixtures thereof.

15. A method of treating or preventing obesity, constipation and paralytic ileus susceptible to amelioration by an alpha$_2$-adrenoreceptor antagonist comprising administering an effective amount of a compound selected from the group consisting of compounds of formula (I), claim 1, physiologically acceptable salts thereof and mixtures thereof.

* * * * *